(12) United States Patent
Balduzzi

(10) Patent No.: US 11,191,738 B2
(45) Date of Patent: Dec. 7, 2021

(54) USE OF TAMOXIFEN FOR THE TREATMENT OF CYSTIC FIBROSIS IN PATIENTS OF BOTH SEXES

(71) Applicant: GB PHARMA S.R.L., Pavia (IT)

(72) Inventor: Giorgio Balduzzi, Pavia (IT)

(73) Assignee: GB PHARMA S.R.L., Pavia (IT)

( * ) Notice: Subject to any disclaimer, the term of this patent is extended or adjusted under 35 U.S.C. 154(b) by 466 days.

(21) Appl. No.: 16/089,528

(22) PCT Filed: Apr. 3, 2017

(86) PCT No.: PCT/EP2017/057895
§ 371 (c)(1),
(2) Date: Sep. 28, 2018

(87) PCT Pub. No.: WO2017/174529
PCT Pub. Date: Oct. 12, 2017

(65) Prior Publication Data
US 2020/0297667 A1    Sep. 24, 2020

(30) Foreign Application Priority Data
Apr. 5, 2016  (IT) .......................... UA2016A002292

(51) Int. Cl.
*A61K 31/138* (2006.01)
*A61K 9/20* (2006.01)
*A61K 9/00* (2006.01)

(52) U.S. Cl.
CPC .......... *A61K 31/138* (2013.01); *A61K 9/0053* (2013.01); *A61K 9/0073* (2013.01); *A61K 9/20* (2013.01)

(58) Field of Classification Search
CPC .. A61K 31/138; A61K 9/0053; A61K 9/0073; A61K 9/20
USPC .......................................................... 514/648
See application file for complete search history.

(56) References Cited

FOREIGN PATENT DOCUMENTS

| WO | 2009105234 A2 | 8/2009 |
|---|---|---|
| WO | 2012134965 A1 | 10/2012 |

OTHER PUBLICATIONS

Coakley et al., "17 beta-Estradiol inhibits Ca2+-dependent homeostasis of airway surface liquid volume in human cystic fibrosis airway epithelia", Journal of Clinical Investigation, 2008, vol. 118, No. 12, pp. 1-11.
Ledford et al., "Tamoxifen takes on cystic fibrosis", Nature Medicine, 2009, vol. 15, No. 1, p. 28.
Gruber et al., "Molecular cloning and transmembrane structure of hCLCA2 from human lung, trachea, and mammary gland", American Journal of Physiology—Cell Physiology, 1999, pp. 1261-1270.
International Search Report and Written Opinion for Corresponding International Application No. PCT/EP2017/057895 (11 Pages) (dated Jun. 12, 2017).

*Primary Examiner* — Kristin A Vajda
(74) *Attorney, Agent, or Firm* — Lucas & Mercanti, LLP

(57) ABSTRACT

The use of tamoxifen or a pharmaceutically acceptable salt as non estrogen-dependent acting drug for the treatment of cystic fibrosis in patients of both sexes is disclosed. Tamoxifen is preferably administered by inhalation route.

2 Claims, 2 Drawing Sheets

USE OF TAMOXIFEN FOR THE TREATMENT OF CYSTIC FIBROSIS IN PATIENTS OF BOTH SEXES

CROSS-REFERENCE TO RELATED APPLICATIONS

This application is a 371 of PCT/EP2017/057895, filed Apr. 3, 2017, which claims the benefit of Italian Patent Application No. UA2016A002292, filed Apr. 5, 2016.

DESCRIPTION

The present invention relates to the use of tamoxifen or a pharmaceutically acceptable salt thereof for the treatment of cystic fibrosis in patients of both sexes and, more in particular to the use of tamoxifen or a pharmaceutically acceptable salt thereof as a drug with a non estrogenic-dependent action for the treatment of cystic fibrosis in patients of both sexes.

Cystic fibrosis is a genetic disease which involves different organs (lungs, pancreas, guts, liver, sudoriferous glands). The lung involvement is the most frequent cause of death and the median survival is 39 years.

Cystic fibrosis is caused by the mutation of a gene codifying for a membrane protein (cystic fibrosis transmembrane conductance regulator—CFTR) which transports the chloride ions through the cellular membrane. At lung level it results that the mucus is denser, it is removed with difficulty and it accumulates in the bronchial tree favouring the development of recurrent pneumoniae which determine a progressive and fatal deterioration of the respiratory functionality.

Cystic fibrosis is a rare disease with an incidence of 0.7 cases every 10000 subjects in Europe. To date there are about 1500 mutations which codify for an abnourmous CFTR. The most frequent is the mutation of F508del/F508del which is present in about 70% of the subjects affected by cystic fibrosis. The mutation F508del/W1282X, present in cells IB3-1, is globally much less frequent.

Numerous active ingredients have been proposed in the last decades for the treatment of cystic fibrosis, even if, being a genetic anomaly, there are no treatments able to restore the normal operation of protein CFTR other than genetic therapy. Notwithstanding researches on the genetic therapy of the cystic fibrosis are ongoing since several years, this important goal has not been reached yet.

The most other farmacological remedies proposed for the treatment of cystic fibrosis are actually indicated for the treatment of specific forms of this pathology, such as the one directed to the respiratory apparatus or to alleviate some symptoms or reduce the risk of complications.

One of the active ingredients proposed for the treatment of cystic fibrosis is tamoxifen. Tamoxifen is a non-steroid molecule capable of selectively modulating the estrogen receptor. Tamoxifen has a mixed agonist/antagonist activity and behaves as agonist or as antagonist depending on the kind of tissue on which it acts. For example, it behaves as agonist on the endometrium and as antagonist on the mammary gland. Tamoxifen is used since ages in therapy as antitumoral in the treatment of mammal estrogen-sensitive tumour.

Its efficacy in the treatment of cystic fibrosis in patients of female sex in fertile age has been suggested by Coakley et al., in J. Clin. Investigation, 118(12), 2008, 1-11 and it has been proven with clinical data in the Italian patent application RM2011A000231 filed in the name of the Applicant on May 9, 2011.

In WO 2009/105234, tamoxifen has been reported in general terms with no experimental supporting data, in a long list of active ingredients wherein the use to treat or improve a disorder associated with a CFTR defect is claimed.

Indeed, WO2012/134965 is related with a method to treat or improve the effects of the diseases characterized by the alteration of the contractility of the smooth muscle cells by administering an association of an inhibitor of CaCC, such as tamoxifen, and a modulator of NKCC.

There is no data in literature that envisages the possibility of using tamoxifen for the treatment of patients of non-female sex affected by cystic fibrosis or that indicates a possible non estrogen-dependent effect of tamoxifen in patients affected by cistic fibrosis.

The Applicant has found that tamoxifen has also a direct estrogen-independent effect, on the Ca-dependent chloride channels determining an increase of the density of the chloride currents and it is therefore useful for the treatment of cystic fibrosis in patients of both sexes.

It is therefore object of the present invention the use of tamoxifen or a pharmaceutically acceptable salt thereof as drug with a non-estrogen dependent action in patients of both sexes for the treatment of cystic fibrosis.

In a particularly preferred aspect of the present invention the pharmaceutically acceptable salt of Tamoxifen is Tamoxifen citrate.

Tamoxifen can be administered by oral systemic route, in particular as tablets as already used in the antitumoral therapy. The marketed tablets contain tamoxifen as citrate salt in doses of 10 mg or of 20 mg.

Other pharmaceutical forms suitable for the oral administration such as syrups, elixirs, capsules, powders and granulates, suspensions can be used.

Administration routes different from the oral administration can also be used for the use object of the present invention. Such administration routes can be the sublingual, intranasal or inhalation route.

The inhalation route is particularly preferred.

For the inhalation route, as for the other parenteral administration routes, it is possible to administer also one of the active metabolites of tamoxifen, in particular 4-hydroxytamoxifen, N-desmethyl-4-hydroxytamoxifen and N-desmethyl-tamoxifen.

The dose of the administered tamoxifen is generally from 10 to 100 mg in one or more doses. Particularly suitable are the daily doses of 60 or of 70 mg.

The formulations contain tamoxifen or a salt thereof in admixture with a suitable pharmaceutically acceptable carrier.

The direct estrogen-independent efficacy of tamoxifen on the Ca-dependent chloride channels has been proven by the Applicant in vitro on the bronchial epithelial cells. The bronchial epithelial cells, besides CFTR, are also endowed with another way which contributes, even if in a minor way, to the chloride transport (Lazarowski and Boucher, Curr Opin Pharmacol 2009, 9(3), 262-7). This way is mediated by P2Y receptors which, stimulated by the ATP present in the bronchial tree, increase the intracellular free calcium ($Ca^{2+}$) (Lazarowski et al., J Biol Chem 2004, 279(35), 36855-64). In its turn, the increase of intracellular calcium activates the Ca-dependent chloride channels.

The Ca-dependent chloride channels are usually present in the patients with cystic fibrosis, but they are relatively inactive (already cited Lazarowski and Boucher).

DESCRIPTION OF THE EXPERIMENTS AND RESULTS

We carried out experiments in vitro (the most reliable and appropriate to assess the effects of a drug in the treatment of CF) in order to assess whether TMX has a direct action on the Ca-dependent chloride channels.

Our experiments were carried out on homozygous CFBE cells leading the F508del/F508 del mutation and on IB3-1 cells (immortalized cell line of bronchial epithelium cystic fibrosis cells, which bring F508del/W1282X mutation).

The chloride currents through the Ca-dependent chloride channels were measured using the patch clamp technique in perforated whole-cell configuration. The whole-cell configuration was obtained not by breaking the membrane below the electrode, but thanks to the action of an ionophore (gramicidin, 10 µg/ml) which, forming pores through the membrane, guarantees electrical continuity between the solution for the electrode and the cytoplasm, while maintaining the cellular integrity. Thus, cytoplasmic components that might be important to the maintenance of channel activity are not removed after dialysis of the cytoplasm with the solution contained in the electrode. In particular gramicidin makes the cell membrane permeable to monovalent cations ($K^+$ and $Na^+$) but not to divalent cations (such as $Ca^{2+}$ and $Mg^{2+}$) and not to anions such as chloride. Therefore the intracellular concentration of divalent cations and chloride are not affected by the dialysis of the cytoplasm.

The solution for the electrode contained (mM): 145 KCl, 1 $MgCl_2$, 10 HEPES, pH 7,25. The solution of the bath in which the cells were put during the experiments were (mM): NMGCl 150, $CaCl_2$ 2, $MgCl_2$ 1, HEPES 10, glucose 10, mannitol 30, pH 7.4. The bath solution was hypertonic (measured osmolarity 337 mOsm) with respect to that of the electrode to inhibit the currents activated by swelling, present in the cells used also in isosmolarity conditions of the bath solution (as noted in previously carried out whole-cell experiments).

Cells (FCS or IB3-1) were incubated for 40 minutes with tamoxifen 5 µM. After this period, the cells were dissolved by experiment, always in the presence of tamoxifen 5 µM.

Figure 1:
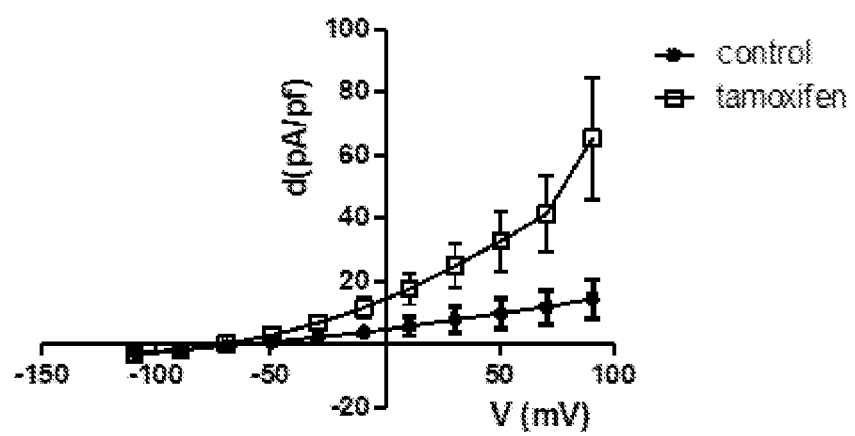
FIG. 1. Current density (d)-voltage (V) relation for the current registered after 40 minutes in CFBE (or IB3-1) cells in absence (control) or presence of tamoxifene 5 µM in the bath solution (n=6). The registered current (pA) has been normalized for the capability of the cell (directly proportional to the cell surface) in order to make the parameter independent from the cell dimensions (and therefore comparable between different cells independently from their surface).

The current density, measured during these experiments, was significantly increased compared to the one observed in control conditions, in favour of the hypothesis that tamoxifen has a direct action on the Ca-dependent chloride channels, increasing the transport of chloride (FIG. 1).

Figure 2:
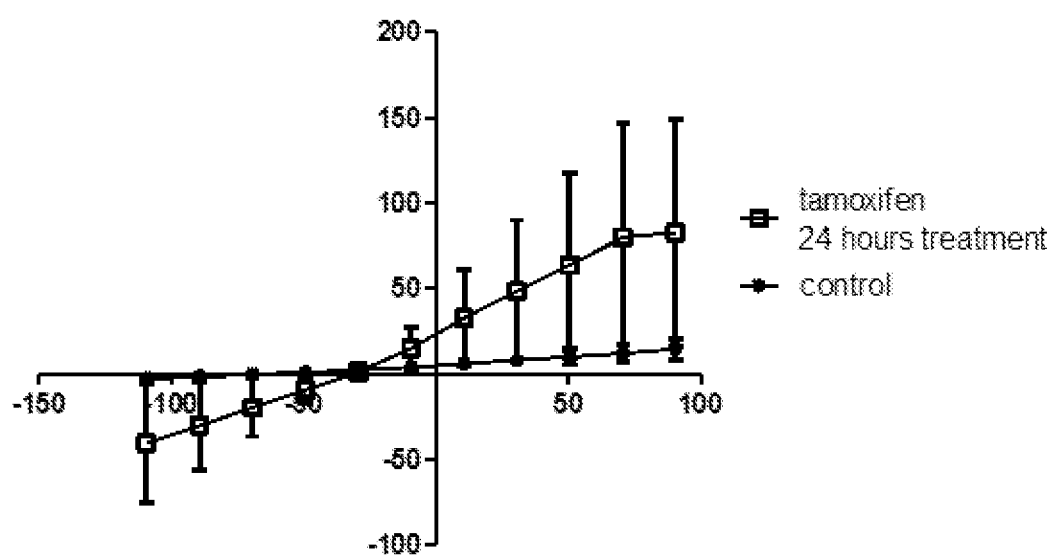
FIG. 2. Current density (d)-voltage (V) relation for the current registered after 24 h in cells IB3-1 in absence (control) or presence of tamoxifen 5 µM in the bath solution (n=6).

Furthermore, to assess a possible long-term effect of tamoxifen on Ca-dependent chloride currents, experiments were carried out using the same cells incubated with 5 µM tamoxifen for 24 hours (FIG. 2).

The obtained data show that the effect of tamoxifen remains almost unchanged over time (24 h, FIG. 2).

Finally, in order to evaluate a possible action of tamoxifen on the CFTR channel, having recorded the I/V in cells treated with tamoxifen for 24 hours, the replacement of the solution with one containing tamoxifen and CFTR inh (specific inhibitor of CFTR) (FIG. 3) was carried out.

Figure 3:
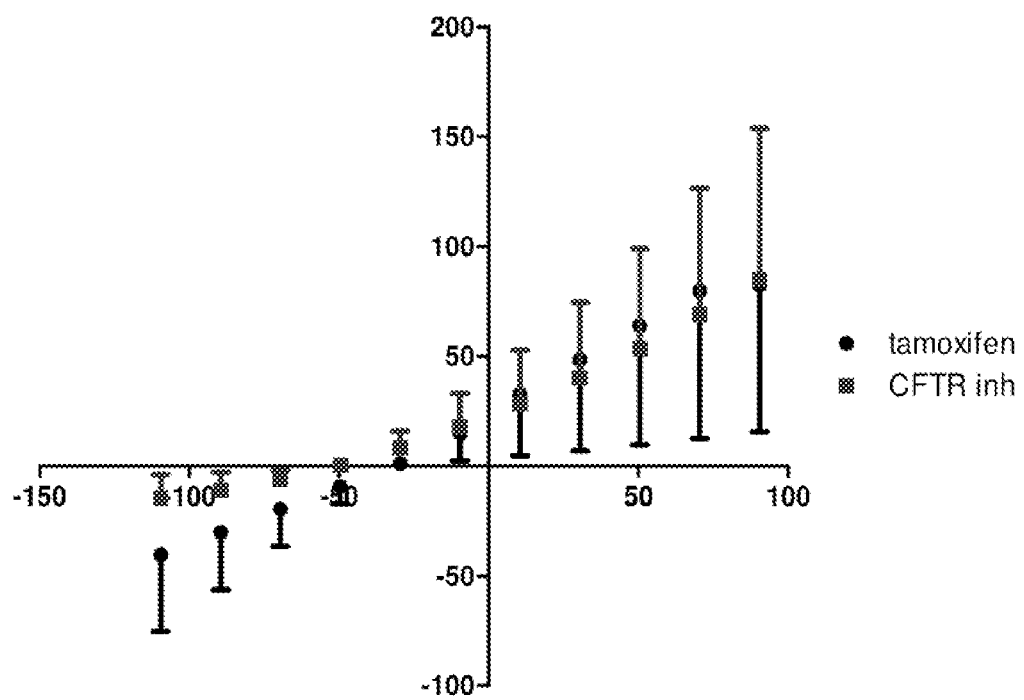
FIG. 3. Current density (d)-voltage (V) relation for the current registered after 24 h in cells IB3-1 in presence of tamoxifen 5 µM, or of tamoxifene+CFTRinh in the bath solution (n=6).

The obtained data show that the effect of tamoxifen on the chloride currents does not change significantly in the presence of the inhibitor of CFTR, indicating that tamoxifen does not act on CFTR channels (FIG. 3).

In conclusion, our experiments show that in cells having mutations responsible for CF, tamoxifen directly acts on the Ca-dependent chloride channels leading to an increase in the density of chloride currents which allows to balance sodium uptake, not allowing its pathological accumulation in the cell and the water recall from mucous secretions which, thus, become viscous.

This action is completely independent from the anti-estrogenic activity of tamoxifen (FIG. 1).

Moreover, the activity of tamoxifen on Ca-dependent chloride channels lasts over time (FIG. 2) and does not involve the CFTR channel activity (FIG. 3).

Therefore tamoxifen can perform its activity in a persistent way every day of the year, both in women and in men.

The invention claimed is:

1. A method of activation of the Ca-dependent chloride channels in a patient having cystic fibrosis, comprising administering an effective amount of tamoxifen or a pharmaceutically acceptable salt thereof as a drug having a non-estrogen dependent action in patients of both sexes to a patient in need thereof.

2. The method of claim 1, wherein said patient is a male.

* * * * *